United States Patent [19]
Tachi et al.

[11] Patent Number: 6,027,247
[45] Date of Patent: *Feb. 22, 2000

[54] X-RAY PHOTOGRAPHING APPARATUS

[75] Inventors: Toshio Tachi, Kashiwa; Akio Hara, Noda; Seiji Kamimura, Kokubunji; Mitsuru Ohnuma; Isamu Takekoshi, both of Tokyo; Michiaki Motoshima, Kashiwa; Hayato Saito, Akita, all of Japan

[73] Assignee: Hitachi Medical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/623,701

[22] Filed: Mar. 29, 1996

[30] Foreign Application Priority Data

| Apr. 4, 1995 | [JP] | Japan | 7-079137 |
| Apr. 4, 1995 | [JP] | Japan | 7-079141 |
| Apr. 4, 1995 | [JP] | Japan | 7-079148 |

[51] Int. Cl.$^7$ .................................................. A61B 6/00
[52] U.S. Cl. ........................ 378/196; 378/209; 378/177
[58] Field of Search .................................... 378/195, 196, 378/208, 209, 167, 177, 179, 193

[56] References Cited

U.S. PATENT DOCUMENTS

| 3,997,792 | 12/1976 | Conrad et al. | 378/177 |
| 4,287,422 | 9/1981 | Kuphal et al. | 378/209 |
| 4,926,456 | 5/1990 | Bock et al. | 378/196 |
| 5,014,292 | 5/1991 | Siczek et al. | 378/196 |
| 5,048,071 | 9/1991 | Van Steenburg | 378/195 |
| 5,097,497 | 3/1992 | Deucher et al. | 378/196 X |
| 5,185,777 | 2/1993 | Hasegawa | 378/177 X |
| 5,185,778 | 2/1993 | Magram | 378/196 |
| 5,222,115 | 6/1993 | Highgenboten | 378/177 |
| 5,231,653 | 7/1993 | Pfeiler et al. | 378/196 X |
| 5,327,474 | 7/1994 | Inoue et al. | 378/196 X |
| 5,475,885 | 12/1995 | Ishikawa | 378/209 |
| 5,572,567 | 11/1996 | Khutoryansky et al. | 378/177 X |
| 5,636,259 | 6/1997 | Khutoryansky et al. | 378/196 X |

*Primary Examiner*—David P. Porta
*Attorney, Agent, or Firm*—Antonelli, Terry, Stout & Kraus, LLP

[57] ABSTRACT

A X-ray photographing apparatus is suitable for use for a doctor to take X-ray photographing while performing medical treatment, and is capable of positioning a patient at a height at which operations are made ease in accordance with contents of medical treatment. The X-ray photographing apparatus comprises a table of a bed, on which a person to be inspected is placed, a table support device having a function for tilting the table about an axis in a direction perpendicular to a longitudinal direction of the bed and vertically moving the bed, a X-ray irradiation device located above the person to be inspected on the bed and spaced a distance from a top side of the table, and a X-ray detection device located below the table, the support device having a horizontal support for supporting the bed from sides of the bed and a vertical support mechanism for vertically moving the horizontal support, and the vertical support mechanism being arranged on one side of the bed and offset toward an end of the bed from a center in the longitudinal direction of the bed, whereby a doctor is not interfered with in smoothly moving and performing medical treatment around a portion of the bed where the upper half of the body of the person to be inspected is placed, and a space for installing other medical treatment tools can be secured.

39 Claims, 14 Drawing Sheets

FIG. 10
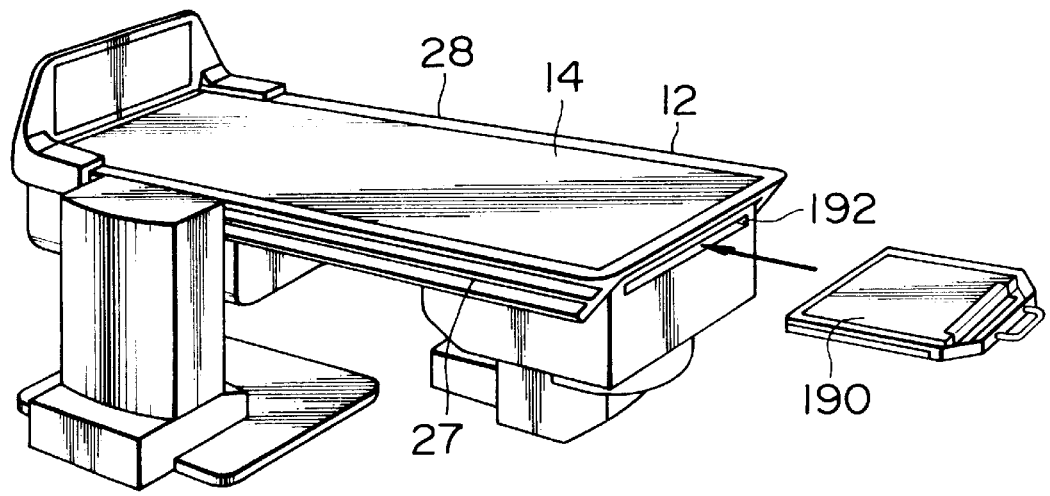
FIG. 11
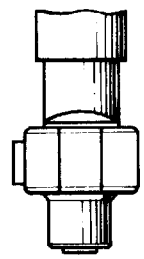
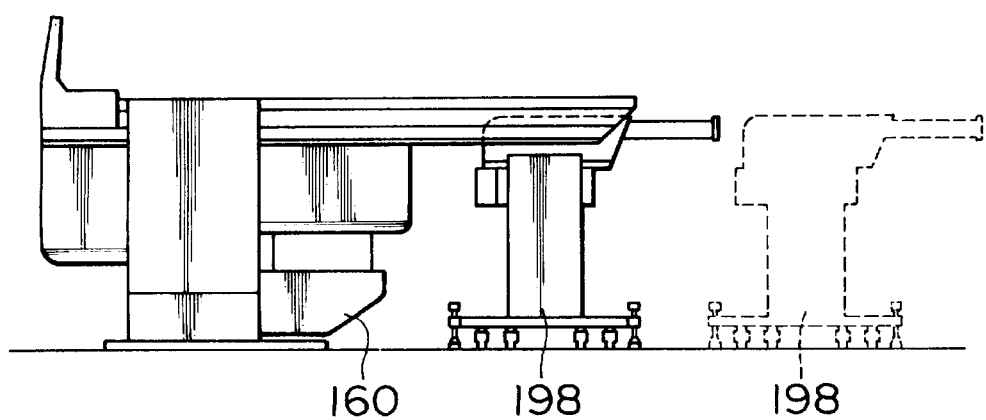

X-RAY PHOTOGRAPHING APPARATUS

BACKGROUND OF THE INVENTION

1. Field of the Invention

The present invention relates to a X-ray photographing apparatus, and particularly to a X-ray photographing apparatus not preventing a medical doctor from moving or performing medical treatment around a bed.

2. Description of the Prior Art

A conventional X-ray photographing apparatus has been used to take X-ray photographing for detection of a disease in its early stages. As the medical science has advanced, not only a request for performing diagnosis but also a request for taking X-ray photographing during medical treatment have been increased and it has been necessary to meet the requests.

A system capable of performing medical treatment and taking X-ray photographing at the same time has not been known for the request for taking X-rays during medical treatment.

SUMMARY OF THE INVENTION

It is an object of the present invention to provide a X-ray photographing apparatus suitable for a medical doctor to take X-rays while performing medical treatment.

It is another object of the present invention to provide a X-ray photographing apparatus capable of positioning a patient at a height where operations can easily performed in accordance with the detail of a medical treatment.

In the X-ray photographing apparatus in one aspect of the present invention, a table support system for rotatably or vertically movably supporting a table of a bed for mounting a person to be inspected has a horizontal support and a vertical support mechanism for vertically moving the horizontal support, and the vertical support mechanism is arranged at one side of the bed to be offset toward an end from the center in the longitudinal direction of the bed. Thereby, it is possible to prevent a bed support system from interfering with medical treatment.

Another X-ray photographing apparatus of the present invention makes it possible to change the bed height in ranges of the minimum height of 850 mm or lower and the maximum height of 870 mm or higher. Thereby, the bed can be kept at a proper position in accordance with the type of operation.

In still another X-ray photographing apparatus of the present invention, the vertical moving speed of a bed is variable and, when a table of the bed is to be inclined, a relatively high speed is selected and the table is raised.

In the present invention, the vertical support mechanism is arranged on one side of a bed to be offset toward an end, for example, legs from the center in the longitudinal direction of the bed. Therefore, a doctor is not interfered with in movement and medical treatment around the bed where the upper half of a patient's body is placed and moreover, it is possible to secure a space in which other medical treatment tools are placed.

BRIEF DESCRIPTION OF THE DRAWINGS

FIG. 10 is an illustration showing how to set a cassette loaded with a film;

FIG. 11 is an illustration showing how to set a film changer substituted for a cassette;

DETAILED DESCRIPTION OF THE PREFERRED EMBODIMENTS

Figure 1:
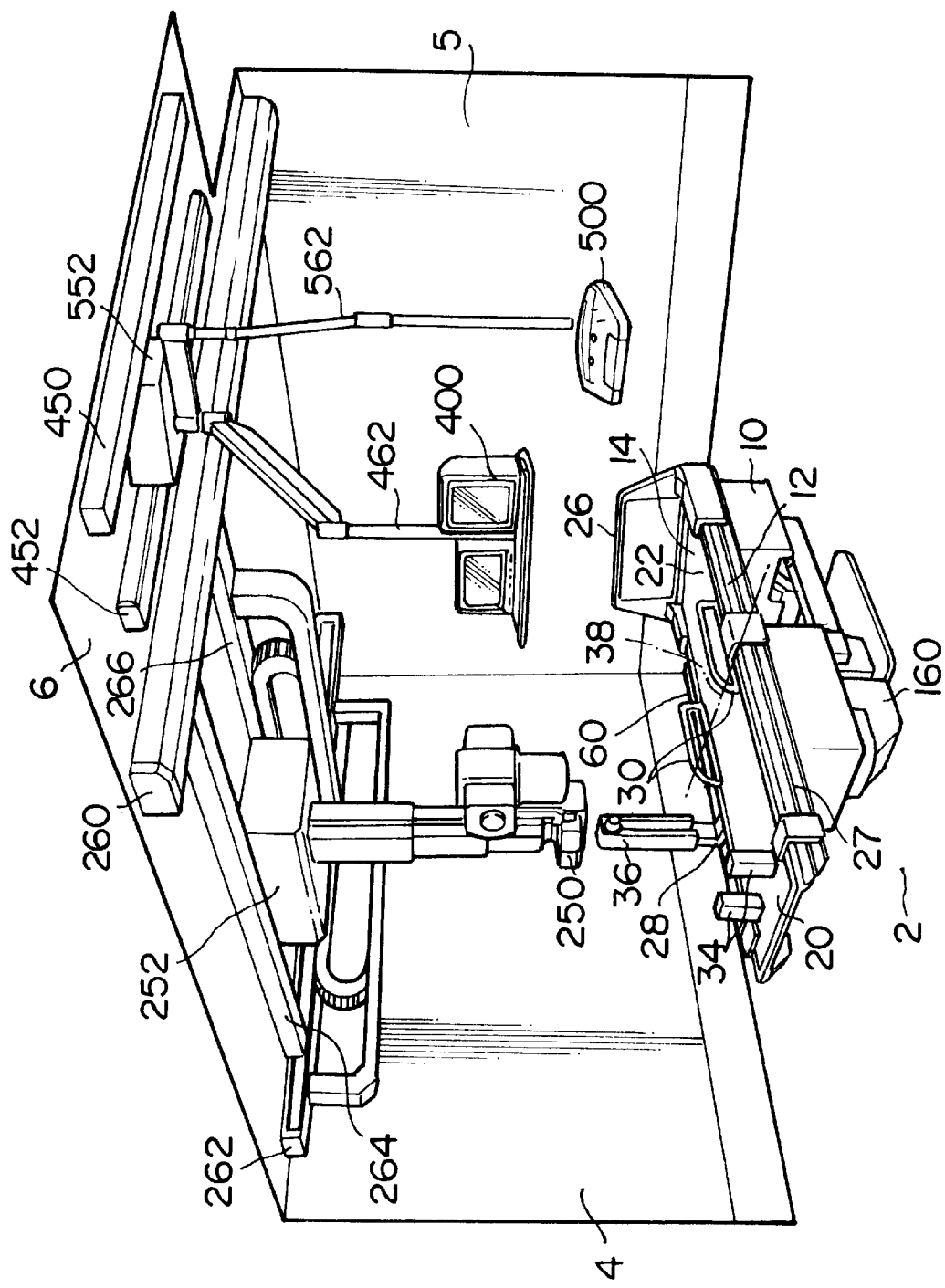
FIG. 1 is an illustration showing the structure of a X-ray photographing apparatus of an embodiment of the present invention having a two-way perspective projection function.
Figure 2:
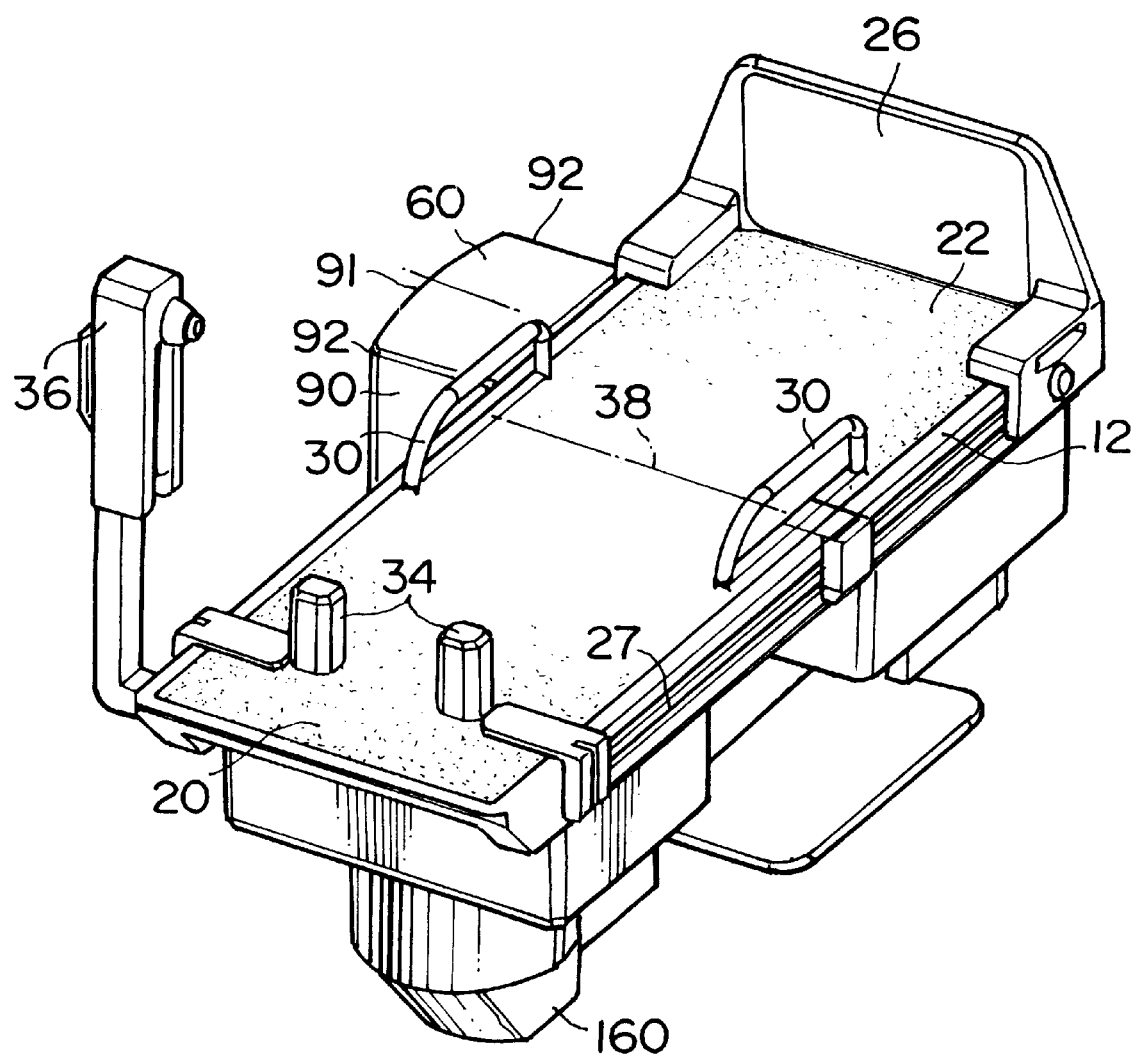
FIG. 2 is an enlarged view illustrating the structure of a bed.

FIG. 1 shows a X-ray photographing apparatus having a two-way perspective projection function, according to an embodiment of the present invention. FIG. 2 is an enlarged view of a bed 10. A table 12 of the bed 10 for mounting a person to be inspected has a top board 14 which is made of a material capable of passing X-rays therethrough. A X-ray irradiation apparatus 250 suspended from a ceiling 6 is arranged a predetermined distance from the top board 14. Moreover, X-ray detection means 160 for detecting X-rays passing through the person to be inspected is provided under the table 12 to take X-rays. An image showing a state of X-ray transmission is formed by the detection means 160 and displayed on a monitor 400. A proximal operator console 500 controls a height and a rotation angle or a tilt angle of the table 12 to keep a position and a direction of the person to be inspected in preferable states, controls the position of the X-ray irradiation apparatus 250, and takes X-rays.

In this embodiment, the bed 10 for mounting thereon a person being inspected is secured to a floor 2 of an inspection room by a support mechanism 60 to be in parallel with walls 4 and 5 of the inspection room. Moreover, the X-ray irradiation apparatus 250 is held by the ceiling 6 through rails 260 and 262 and a support carriage 252 for movement. The monitor 400 and the proximal operator console 500 are held by rails 450 and 452 provided on the ceiling 6 in the inspection room through arms 462 and 562 and a support carriage 552 used in common. The above structure and arrangement make it possible to arrange the X-ray irradiation apparatus 250, monitor 400, and proximal operator console 500 separately from the bed 10. Thereby, when taking X-rays of the person to be inspected while remedying the person, there are advantages that the circumference of the bed 10 is opened, the medical treatment by a doctor is less interfered with and the doctor can easily move and approach the person to be inspected. Moreover, it is possible to achieve objects and advantages in easily securing a space in which other medical treatment tools are placed. Furthermore, since the support mechanism 60 is arranged on the wall side of the bed, it is possible to effectively secure a space for medical treatment by the doctor. Furthermore, since the height of the support mechanism 60 is made lower than the top board 14 of the bed 10 during medical treatment, it does not interfere with medical treatment by the doctor.

The table 12 of the bed 10 is opened on its head side 20 and a footrest 26 is provided on a leg side 22 of the table 12. When the table 12 of the bed 10 is rotated to be upright, the footrest 26 approaches the floor 2, so that a person to be inspected puts his legs on the footrest 26 and stands with his back on the top board 14 of the table 12 and thereafter, the person to be inspected is set to a desired position and direction by making the table horizontal. Rails 27 and 28 are mounted to the both sides of the bed 10 respectively, and accessories such as grips 30, shoulder guards 34, and a compression cylinder 36 are mounted to the rails 27 and 28, as desired. These accessories can be moved to positions conformed to the person to be inspected along the rails 27 and 28. Because the rails 27 and 28 are secured to not top surfaces on the both sides of the table 12 but the sides of the table 12 due to the thickness of the table 12, it is unnecessary to provide spaces of a width corresponding to the rail interval on the both sides of the table 12, the width of the bed can be decreased, and therefore there are an object and an advantage in facilitating a doctor performing medical treatment and inspections. Moreover, since rails formed with grooves are displaced from the top surfaces of the table to the side surfaces thereof, there are an object and an advantage in facilitating wiping off barium, blood, or other chemicals from the top surfaces of the table. The support mechanism 60 is provided offset toward an end of the table 12 from the center 38 along the length of the table 12, so that there are an object and an advantage in enabling eliminating obstacles to the movement of the doctor and arrangement of tools necessary for movements and medical treatment afforded by the doctor around the bed 10 as much as possible. In this embodiment, the mechanism 60 is offset toward the head side 20 of the bed 10 rather than the leg side 22. A person to be inspected is frequently treated for the upper half of the person's body and the person's head. Therefore, in this embodiment, there are an object and an advantage in that the head side from the center 38 of the bed 10 can be opened. The cover or the casing 90 of the support mechanism 60 is rounded at the respective corners and is curved at its opposite side to the bed so as to decrease a thickness of the both sides 92 of the casing 90 compared to a distance of a central portion 91 from an end of the table. This prevents obstacles from interfering medical treatment as much as possible and protects doctors or nurses from being injured due to collision with the case.

Figure 3:
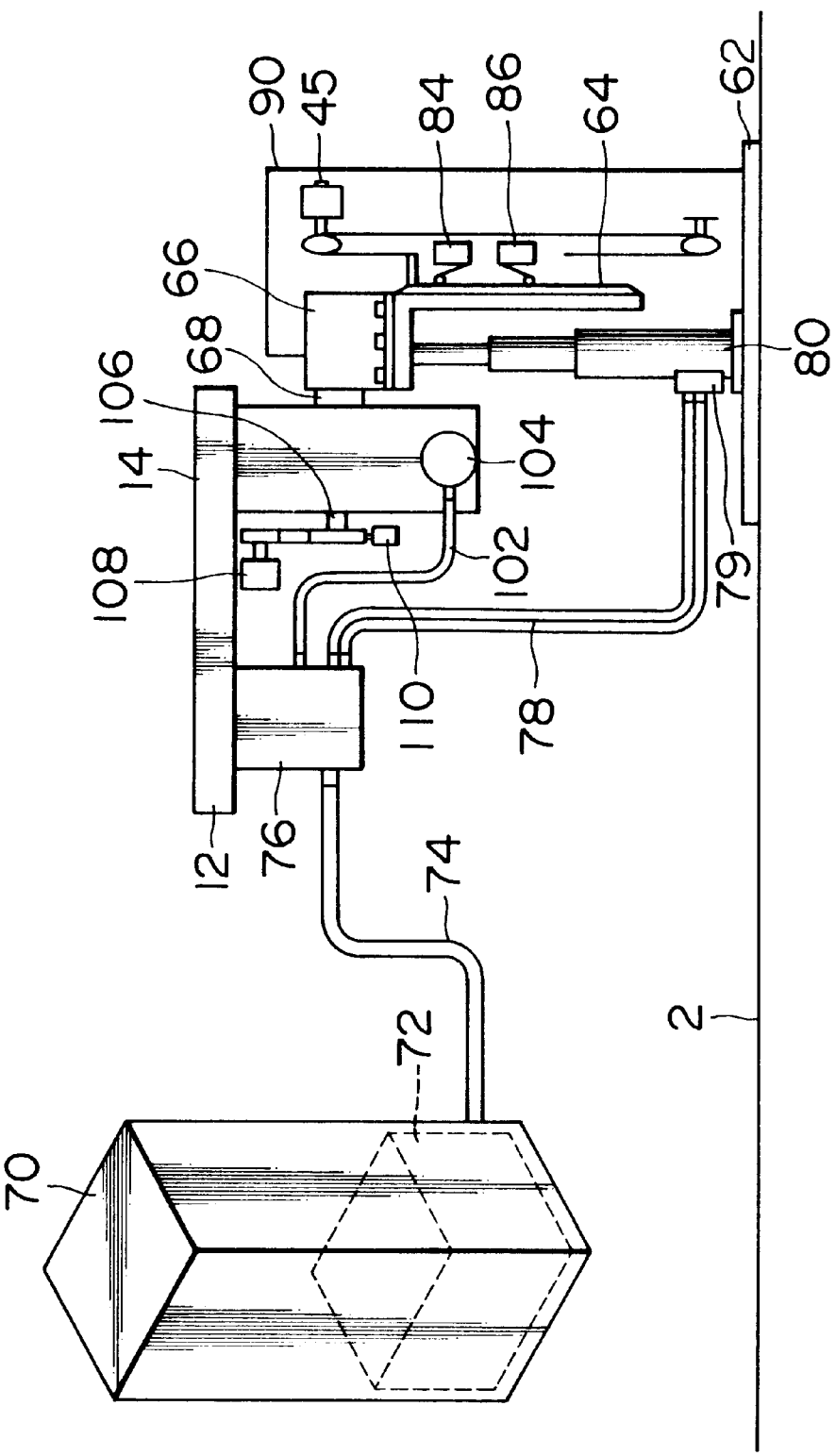
FIG. 3 is an illustration showing the structure of a control mechanism for controlling a position of a bed.

FIG. 3 is an embodiment showing a mechanism for controlling vertical movement and rotation or inclination of the table 12. A floor bed 62 is secured to the floor 2 of the inspection room by four anchor bolts. A hydraulic cylinder 80 is secured to the floor bed 62 to vertically move a horizontal support 68 for supporting the table 12. The horizontal support 68 is secured to the top end of the vertically-moving cylinder 80 by a vertically-moving frame 64 and a horizontal-support securing system 66. An encoder 45 for detecting an absolute height attained by vertical movement detects a height of the top board 14 of the table 12 in accordance with movements of a belt secured to the vertically-moving frame 64. Moreover, a downward overrun switch 84 for detecting downward overrun and an upward overrun switch 86 for detecting upward overrun are provided so that upward or downward movement does not exceed an safety range. The whole of these equipments functions as a bed support mechanism and they are covered with the casing 90.

The hydraulic cylinder 80 is of a three-stage telescopic type and its driving oil pressure is produced by a hydraulic unit 72 of a control box 70, sent to a valve unit 76 computer-controlled through a pipe 74, transmitted to a check valve 79 via a pipe 78 from the valve unit 76, and applied to the hydraulic cylinder 80. Because a hydraulic cylinder is used, there are an object and an advantage in that the whole of a bed support mechanism becomes small-sized and the circumference of a bed is further opened. Moreover, there are an object and an advantage in that combination of the hydraulic cylinder 80 and the vertically-moving frame 64 makes it possible to decrease a width of the table support mechanism and a thickness of the casing 90 covering the cylinder 80 and the frame 64, and they do not so much interfere medical treatment by a doctor even if they are located at the side of the table. The check valve 79 functions to be closed for disconnecting the piping 78 from the cylinder 80 so that hydraulic pressure in the cylinder 80 does not lower if the pressure in the piping 78 is lowered due to any trouble. Thereby, there are produced an object and an advantage in that the table can be prevented from lowering due to the above trouble and safety can be secured. Moreover, even if an operational error occurs in lowering or raising the table, there is an advantage in that safety can be maintained because movements exceeding a safe moving range are detected by the overrun switches 84 and 86 and the computer automatically controls the valve unit 76 in accordance with outputs of the switches to stop upward or downward movement.

Rotation or tilting of the bed is controlled by a rising-falling hydraulic motor 104. A predetermined hydraulic pressure is fed to the rising-falling hydraulic motor 104 via the pipe 74, valve unit 76, and pipe 102. The motor 104 is adapted to be rotated by the applied hydraulic pressure. The rotation of the motor is transmitted to a worm gear transmission 106 to change an angle to the horizontal support 68, and so the table 12 turns about the horizontal support 68. The rotational directions are changed by switchover of the valve unit 76. A rotation angle is detected by a rising-falling encoder 108 and overrun of rotation is detected by a rising-falling overrun switch 110. Because tilting of the table is controlled by the hydraulic motor 104, there is an advantage in that the whole apparatus becomes small-sized. The motor 104 is provided with a reduction gear 106. Because reduction gear 106 is provided with a self-locking function, the rotation of the motor 104 is locked by the reduction gear 106 when the hydraulic pressure in the pipe 102 becomes abnormal due to any reason, so that the tilting of the table does not change. Thereby, there is an advantage in that safety can be maintained.

Figure 4:
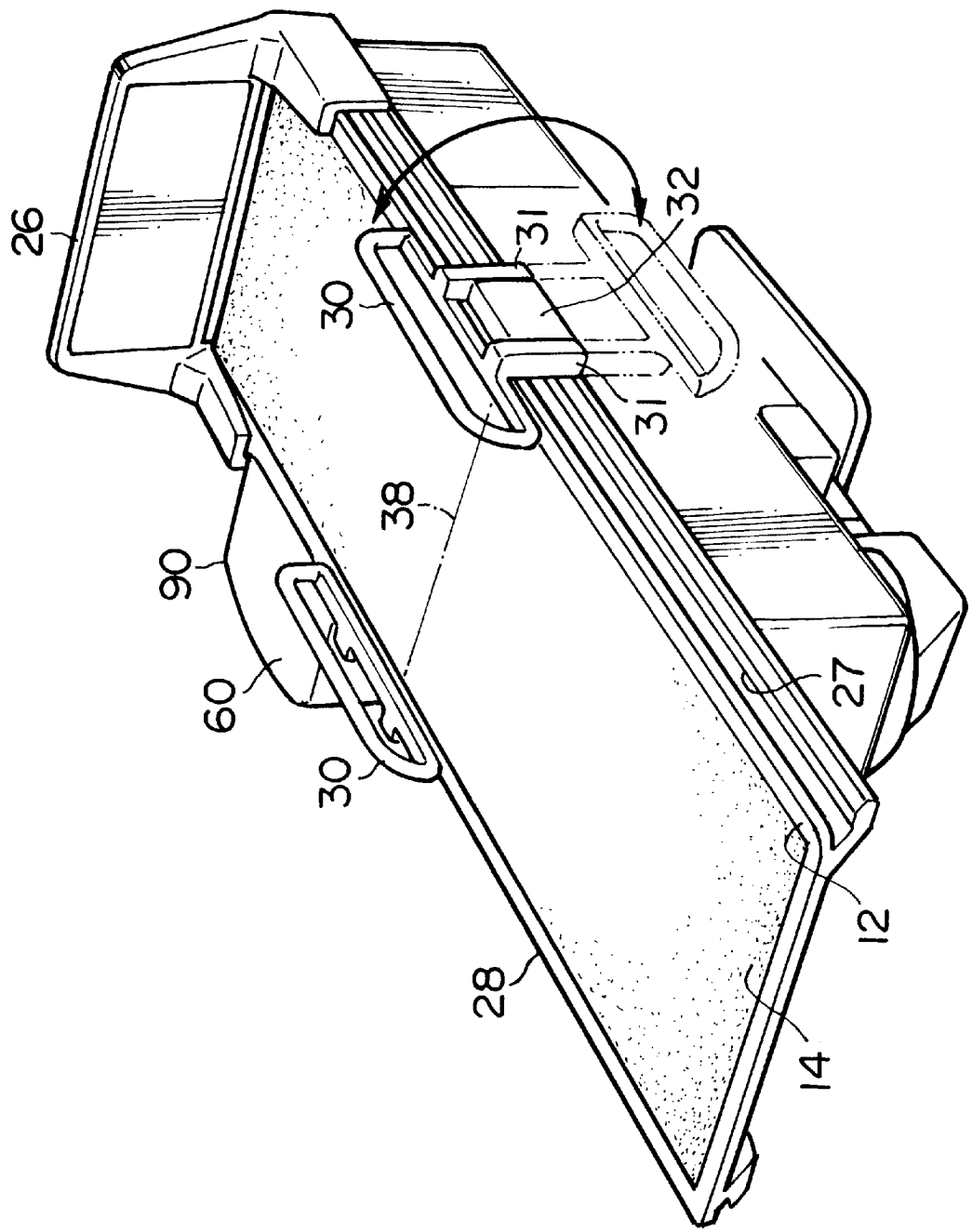
FIG. 4 is an illustration showing the structure of grips of a bed.

FIG. 4 is an illustration of the grips 30 of the bed. The grips 30 are removably mounted to the rails 27 and 28 on the both sides of the table respectively by securement devices 32. The grip 30 has grip legs 31. The grip legs 31 constructed to interpose therebetween the locking device 32 are rotatably mounted to the sides of the locking device 32. When a doctor rotates the grips 30 on the both sides to above the top of the table 12, the side surfaces of the grip legs 31 facing the table contact the surfaces of the rails 27 and 28 to be fixed. In the case where the grips 30 are in the way when moving a person to be inspected from a stretcher to the top board, the grips are opened outwards to rotate the connection between the grip legs 31 and the locking device 32, so that the grips are made to fall. Moreover, the grip is received under the table to be positioned inward from the rail surface corresponding to the side surface of the table by an extent where the bottom surface of the grip 30 contacts the top board surface of the rail. Therefore, there is an advantage in that the grips are not in the way. Moreover, portions of the grips toward the head side of the table are inclined at, for example, approx. 45° to be contiguous to lower portions of the grips. A person to be inspected can easily grasp the inclined portions of the grips with his strength when the person is positioned with his head directed downwards in X-ray photographing, so that it is possible to reduce uneasiness which would conventionally cause the person to feel that he might slip down the table. Portions of the grips toward the end of the table where the person's legs are located may be at around 90° as usual rather than inclined.

Figure 5:
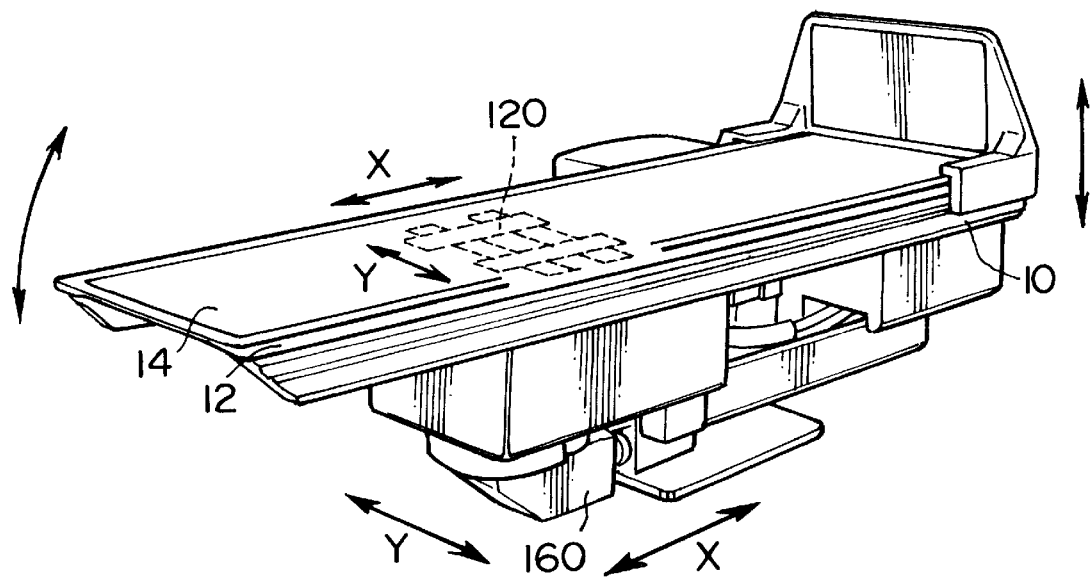
FIG. 5 is an illustration showing the control of a diaphragm mechanism for executing a X-ray masking function.
Figure 6:
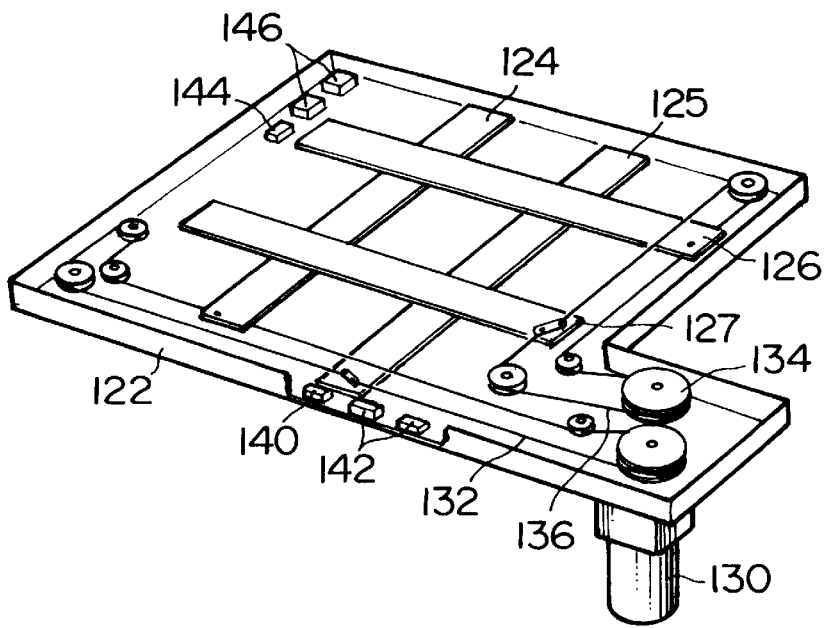
FIG. 6 is an illustration showing the control of a diaphragm mechanism for executing a X-ray masking function.

FIGS. 5 and 6 show a control of a diaphragm mechanism 120 which provides a X-ray masking function. The table 12 of the bed 10 is provided with the top board 14 serving as an upper plate and the diaphragm mechanism 120 having the masking function below the board 14. As shown in FIG. 5, the table 12 can rotate as shown by an arrow, the diaphragm mechanism 120 can move in X and Y directions, and the imaging device 160 can also move in the X and Y directions.

The diaphragm mechanism 120 comprises lengthwise dividing masks 124 and 125 movably mounted to a diaphragm mechanism frame 122, widthwise dividing masks 126 and 127, a lengthwise mask motor 130 and a wire rope 132 for moving the lengthwise dividing masks 124 and 125, a widthwise mask motor 134 and a wire rope 136 for moving widthwise dividing masks 126 and 127, and origin detecting sensors 140 and 144 for detecting an origin of the lengthwise dividing masks 125 and 126, respectively, and overrun sensors 142 and 146 for detecting overrun.

Because X-ray irradiation is harmful for a human body, it is necessary to limit an irradiation range of X-rays to only necessary portions. Though the X-ray irradiation is restricted in area by a X-ray irradiation system, it is desired to take X-ray photographing of only necessary portions. Therefore, the lengthwise mask motor 130 and the widthwise mask motor 134 are controlled by a console 500 to be mentioned later so that an area surrounded by the lengthwise and widthwise masks 124, 125, 126, and 127 is controlled to a preferable value and a position. Thus there are produced an object and an advantage in that X-rays are prevented from scattering and an image quality is improved. To improve a control accuracy, the motors 130 and 134, respectively, comprises a DC motor. Here, a lengthwise direction corresponds to a X direction and a widthwise direction corresponds to a Y direction in FIG. 5.

Figure 7:
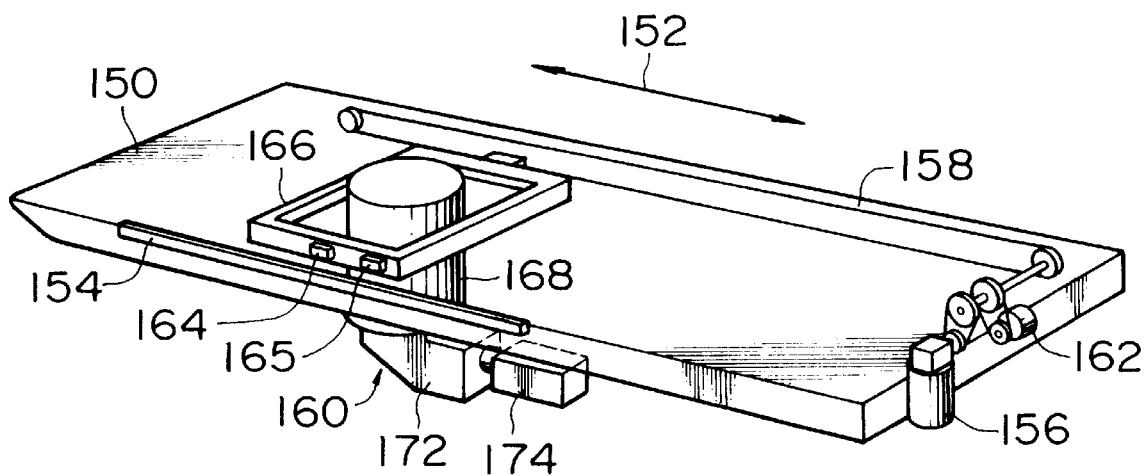
FIG. 7 is an illustration showing the structure of an imaging mechanism serving as X-ray detection means.

FIG. 7 shows an imaging mechanism 160 disposed below the bed 10. There are provided rails 154 for holding the imaging mechanism 160 on the both inner sides of a support frame 150 provided below the table 12 and making the mechanism 160 movable in the Y direction shown by an arrow 152. FIG. 7 shows only one side. In this embodiment, the term "rail" is used in a very wide meaning. For example, one which is not of a convex structure but comprises a concave-shaped groove extending lengthily and by which the mechanism 160 is guided is described as a rail. In FIG. 7, the imaging mechanism 160 held by the rail 154 is positionally controlled by a motor 156 secured to the support frame 150 and a chain 158 for transmitting the rotation of the motor 156 to move the imaging mechanism 160 along the rail 154. A signal indicative of a value of the position is detected and generated by an absolute-value sensor 162. Moreover, to prevent the movement of the imaging mechanism 160 in the Y direction from exceeding a safety range, two overrun switches 164 and 165 for detecting the movement exceeding a predetermined range are provided on an image-system moving frame 166.

Figure 8:
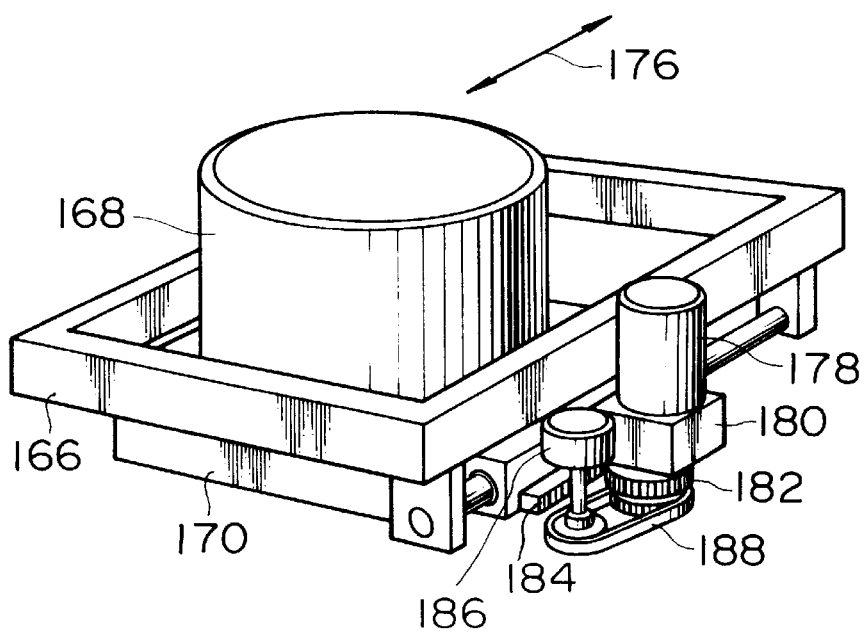
FIG. 8 is an enlarged view showing the structure of an image receiving unit of an imaging mechanism.

An image receiving unit 168 for converting X-rays into light of intensity corresponding to the intensity of the X-rays is mounted to the image-system moving frame 166 through a mounting frame 170. Light produced by the image receiving unit 168 is conducted to a camera 174 through an optical path 172. A X-ray image detected by the camera 174 is displayed on a monitor 400 and is operatively recorded and photographed. FIG. 8 is an enlarged view showing the image receiving system 168. Movement of the imaging system 168 in the X direction shown by a arrow 176 in FIG. 8 is controlled by a motor 178 secured to the moving frame 166, reduction gear 180, a rack 184 secured to the mounting frame 170, and a pinion 182 engaged with the rack 184 and rotated by the reduction gear 180. The moving frame 166 is generally moved by the motor 156 and the chain 158 in the X direction and the imaging system 168 is moved in the moving frame 166 in the Y direction by the pinion 182 and the rack 184 due to the rotation of the motor 178. The position of the imaging system 168 in the Y direction is detected by an absolute value sensor 186, to which the rotation of the pinion is transmitted through a belt 188. Because the imaging system is moved by the above mechanism, moving devices in the X and Y directions can be made small-sized and thin to reduce restrictions to the height of the bed. Therefore, even if the table 12 is lowered as needed, it does not contact with the floor of the inspection room. Thus, when photographing while performing medical treatment, it is possible to keep a patient on the table at a height which makes medical treatment easy. Moreover, these devices are located below the bed but they do not protrude beyond the periphery of the table, so that a space for other medical treatment tools can be secured and movements of doctors and nurses are not hampered.

Figure 9:
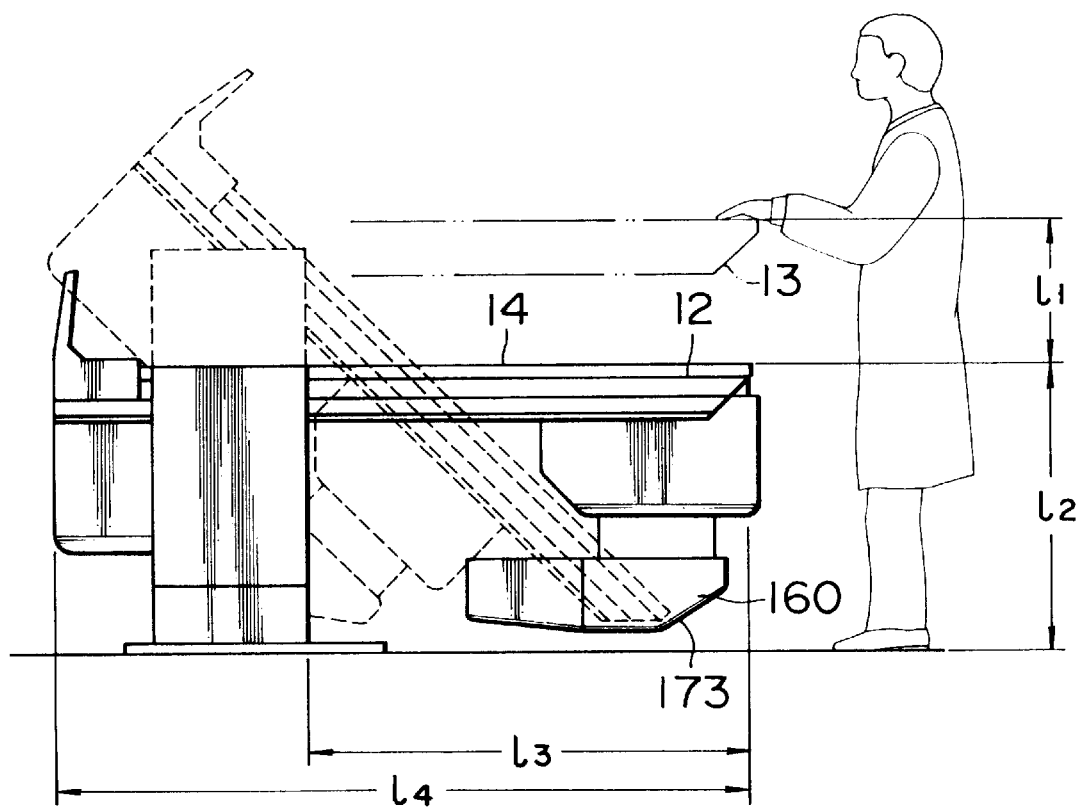
FIG. 9 is an illustration showing a state in which a doctor applies medical treatment to a patient.

FIG. 9 is an illustration showing a state in which a doctor performs medical treatment or a state in which the head of a person to be inspected is made lower than his leg in X-ray photographing. If the table 12 is too low, a doctor must bend his knees when applying medical treatment to the person to be inspected and therefore, the doctor cannot perform complete medical treatment. However, even if the table 12 is too high, medical treatment cannot smoothly be performed. Therefore, in medical treatment, it is desired to set a height L2 of the top board 14 which defines a top surface of the table 12 to 800 mm or more and its height adjusting range L1 to approx. 400 mm. Accordingly, it is desired that the height of the top board from the floor varies in a range of 800 to 1200 mm. If the top end of the support mechanism 60 of the table 12 became higher than the top board 14 when the top board 14 is lowered, medical treatment would be hampered. Therefore, the cylinder 80 in the support mechanism 60 comprises a three-stage cylinder whereby the height of the cylinder when contracted is set low. Moreover, since the height of the imaging mechanism 160 is set low, it is possible to lower the table 12. Speed of the vertical movement of the table is not constant but variable. This is because there can be a choice whether the table should be moved slowly in accordance with the condition of the person's health or quickly in order to quickly finish taking X-rays. Moreover, it is possible for a doctor or an inspection technician to select one among a plurality of moving speeds which are previously set. This makes it possible to reduce a doctor's load such that the doctor can concentrate on medical treatment such as a surgical operation.

In FIG. 9, broken lines show the table 12 being rotated in a direction, in which the head of the person is lowered. This operation is performed by a remote or proximal operator console. When an instruction for this operation is issued, the table and the support mechanism 60 automatically rise up to a predetermined height and the head side of the table lowers. In this case, the table rising speed is set higher than the table tilting speed. In the case where it is possible to set a plurality of speeds for the rising speed, the table automatically rises at a speed higher than the minimum rising speed in order to tilt the table as quickly as possible. That is, in taking X-ray photographing of stomach states, the person's head may be operatively lowered. However, a period of time for taking X-ray photographing cannot be extended so much because of the state of barium in the stomach. The purpose is to compensate for the above state.

An underside 13 of the head-side end portion of the table 12 is cut to approx. 45° in order to prevent the table from abutting against the floor even when tilted as shown in FIG. 9. Moreover, an underside 173 of the head-side end portion of the imaging mechanism 160 is similarly cut in order to prevent the mechanism from abutting against the floor. As seen from FIG. 9, the support mechanism 60 of the table 12 is provided toward the leg side from the center in the longitudinal direction of the table in order to prevent the mechanism 60 from interfering with movements of a doctor in medical treatment for the head to the abdomen of a person to be inspected and secure a place where medical treatment tools are installed, as widely as possible.

FIG. 10 illustrates insertion of a film called a cassette 190. The film is sensitive to X-rays and shows a shade of black color depending upon the X-ray intensity. The film stored in a case is called a cassette. The cassette 190 is inserted under the top board 14 and the diaphragm mechanism 120 of the table 12 from an inserting port 192 and inserted into the support frame 150 which forms the bottom of the table 12. The table 12 is provided with the relatively hard top board 14 and the rails 27 and 28, of which both sides mount thereto accessaries, and the inside of the table 12 permits insertion of the cassette 190, receives the diaphragm mechanism 120, and has the image receiving unit 168 of the imaging system depending therefrom. While these devices are broken when they collide with other device, they are protected by the sides of the table 12, to which the top board 14 and the rails 27 and 28 are mounted.

FIG. 11 is an illustration showing the use of a film changer 198 for automatically changing a X-ray sensitive film for another one for photographing several X-ray images in place of the imaging mechanism 160. The imaging mechanism 160 is moved to the leg side portion of the table 12 by means of the proximal operator console 500. This movement is performed by the moving motor 156 along the rails 154 on the support frame 150 at the bottom of the table. The film changer 198 is provided at its underside with wheels for movement to be conducted inside the rails 154 on the both sides of the support frame 150 for continuous photographing. With this arrangement, insertion of the film changer 198 can be simplified and moreover performed in a short time.

In FIG. 1, the X-ray irradiation system 250 is movably suspended by the X-direction rails 260 and 262 secured to the ceiling 6 and the Y-direction rails 264 and 266 held by the rails 260 and 262. The X-direction rails 260 and 262 are secured to the ceiling above the bed 10 in the X direction corresponding to a longitudinal direction of the bed 10. While moving along the X-direction rails 260 and 262, the X-ray irradiation system 250 moves in the X direction which corresponds to the longitudinal direction of the bed 10. Moreover, the Y-direction rails 264 and 266 movably supported by the rails 260 and 262 are parallel with the Y direction which corresponds to a direction along the short side of the bed 10. Therefore, while moving along the Y-direction rails 264 and 266, the X-ray irradiation system 250 can move along the Y direction of the bed 10.

In this specification, the term "rail" is used in a very wide meaning such that not only a long convex rail but also a long concave guide, by which the system 250 is guided, are expressed as rails.

Figure 12:
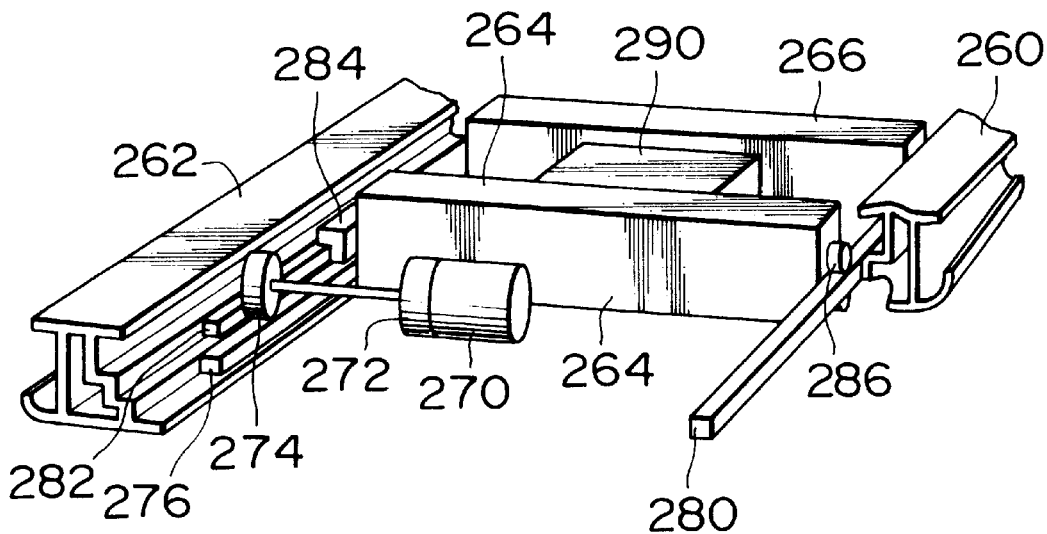
FIG. 12 is an illustration showing the structure of a moving mechanism of a X-ray irradiation apparatus.
Figure 13:
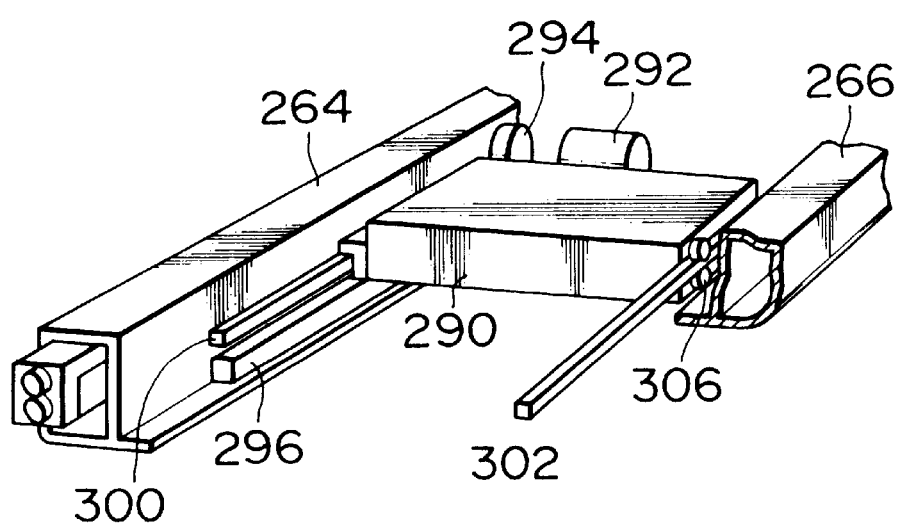
FIG. 13 is an illustration showing the structure of a moving mechanism of a X-ray irradiation apparatus.

FIGS. 12 and 13 show moving mechanisms movable in the X-direction and the Y direction. An X-direction motor 270 is secured to the Y-direction rail 264 and the rotational driving force of the X-direction motor 270 is transmitted to a pinion 274 which engages with racks 276, respectively, provided on the X-direction rails 260 and 262 through a harmonic reduction gear 272. By controlling the rotational direction and speed of the X-direction motor 270, it is possible to control the moving direction and speed of the Y-direction rails 264 and 266. Guide rails 280 and 282 are provided on the X-direction rails 260 and 262, respectively. Guide wheels 286 provided on the Y-direction rails 264 and 266, respectively, are moved along the guide rails 280 and 282 by the X-direction motor 270 to move the Y-direction rails 264 and 266. The guide wheels 286 on the both rails 264 and 266 are covered with an LM guide 284.

FIG. 13 is an illustration showing movements of a box 290 relative to the Y-direction rails 264 and 266. A rack 296 is provided on the Y-direction rail 264, a pinion 294, to which rotation is transmitted from a motor 292 secured to the box 290 through a reduction gear, engages with the rack 296 so that the box 290 is moved in accordance with the rotational direction and speed of the motor 292. Moreover, guide rails 300 and 302 are provided inside the X-direction rails 264 and 266, respectively, along which guide wheels 306 provided on the box move. A X-ray irradiation apparatus is suspended from the box 290.

Though not illustrated in FIG. 12 or 13, microswitches are provided on the Y rail and the box 200 to detect the box coming off a safety area to send a signal to a computer (not shown) for alarming and automatic stoppage. A travelling carriage 252 in FIG. 1 houses the motors, reduction gears 270, 272 and 292, and the box 290 shown in FIGS. 12 and 13. The above structure makes it possible to simplify movements of a X-ray irradiation section in the X and the Y directions and smoothly move the X-ray irradiation section and the imaging section to a predetermined relation without moving a bed. Therefore, necessary X-rays can be obtained. Moreover, the bed is not moved in the X or the Y direction, so that medical treatment tools can be mounted and load on a patient can be reduced. Control motors comprise DC motors and therefore, it is possible to minutely control the speed and direction.

Then, the proximal operator console 500 is described below. Though mentioned later, a control panel is provided in another room in order to protect a doctor and a X-ray technician from exposure to X-rays, and it is common to operate the control panel while conversing with a person to be inspected on the other side of a window by using a unit such as a microphone. However, owing to advancement of medical science, it has been necessary to confirm a condition inside of the body of a person to be inspected and a state and position of a medical treatment tool inserted into the body by means of X-rays while performing a surgical operation or medical treatment such insertion of the medical treatment tool into a vein of the person. Therefore, a proximal operator console which can immediately be operated on the spot while performing the above medical treatment or surgical operation has become indispensable in addition to the original control panel in another room.

The proximal operator console is described below by referring to FIGS. 14, 15, and 16. The proximal operator console 500 is shaped to be narrow at the front side and wide on the back side so that the front or rear of the console can be recognized at a glance. This is because a doctor or nurses can concentrate on other works such as medical treatment. A casing 510 having the above shape is covered with a soft material such as foamed urethane so that the doctor or nurse is not injured even if he or she touches or collides with the console while concentrating on other works. Moreover, four corners 514, 515, 516, and 517 of the casing 510 are rounded to have a radius of 5 mm or more, preferably 20 mm or more in view of the above objects and advantages. In this embodiment, the corners 514 and 517 are rounded at a radius of 30 mm and the corners 515 and 516 are rounded at a radius of 50 mm. Because a grip 512 is provided at the front side to be used to pull the console. Moreover, a transverse slot 520 with a width of 30 to 50 mm is formed on the back side of the grip 512. It is possible to move the console back and forth, right and left, or up and down only by inserting a hand into the slot 520 without holding the grip 512. Corners 522 on the back side of the slot are also rounded at a radius of 15 mm. However, since the corners are not convex but concave, it is enough for the radius to be small. Therefore, there is an advantage that blood or chemicals can easily be wiped away from the corners 522. There are many operating switches, joy sticks, and displays in the casing 510.

Figure 15:
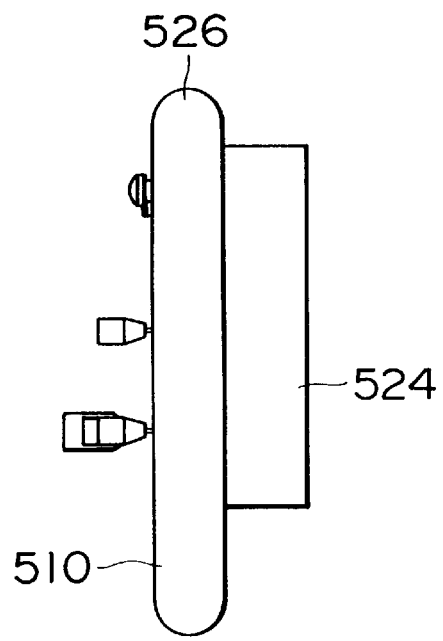
FIG. 15 is a side view showing the structure of a proximal operator console.
Figure 16:
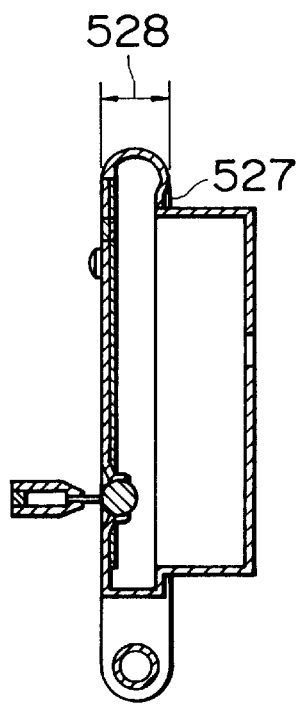
FIG. 16 is a sectional view showing the structure of a proximal operator console.

FIG. 15 is a side view of the casing 510 and FIG. 16 is a sectional view of the casing. There are switches and joy sticks at the center of the casing 510 and there is a back lid 524 on the back surface of the casing. The back lid 524 is held by an arm suspended from the ceiling and a base having wheels to be mentioned later. The back lid 524 is small as compared with the casing 510 and the circumference of the casing is curved and therefore, the casing can easily be held. In this embodiment, the circumference 526 is defined by a curved surface similar to a circle. To form a grip, there is formed a concave groove 527 on the back surface of the casing. It is desired to set a thickness 528 to 20 to 60 mm so as to easily move the proximal operator console. Joy sticks are arranged in a projection plane of the back lid 524. The problem relating to dimensions of detection sections of the joy sticks is accommodated for by the thickness of the back lid 524.

Figure 14:
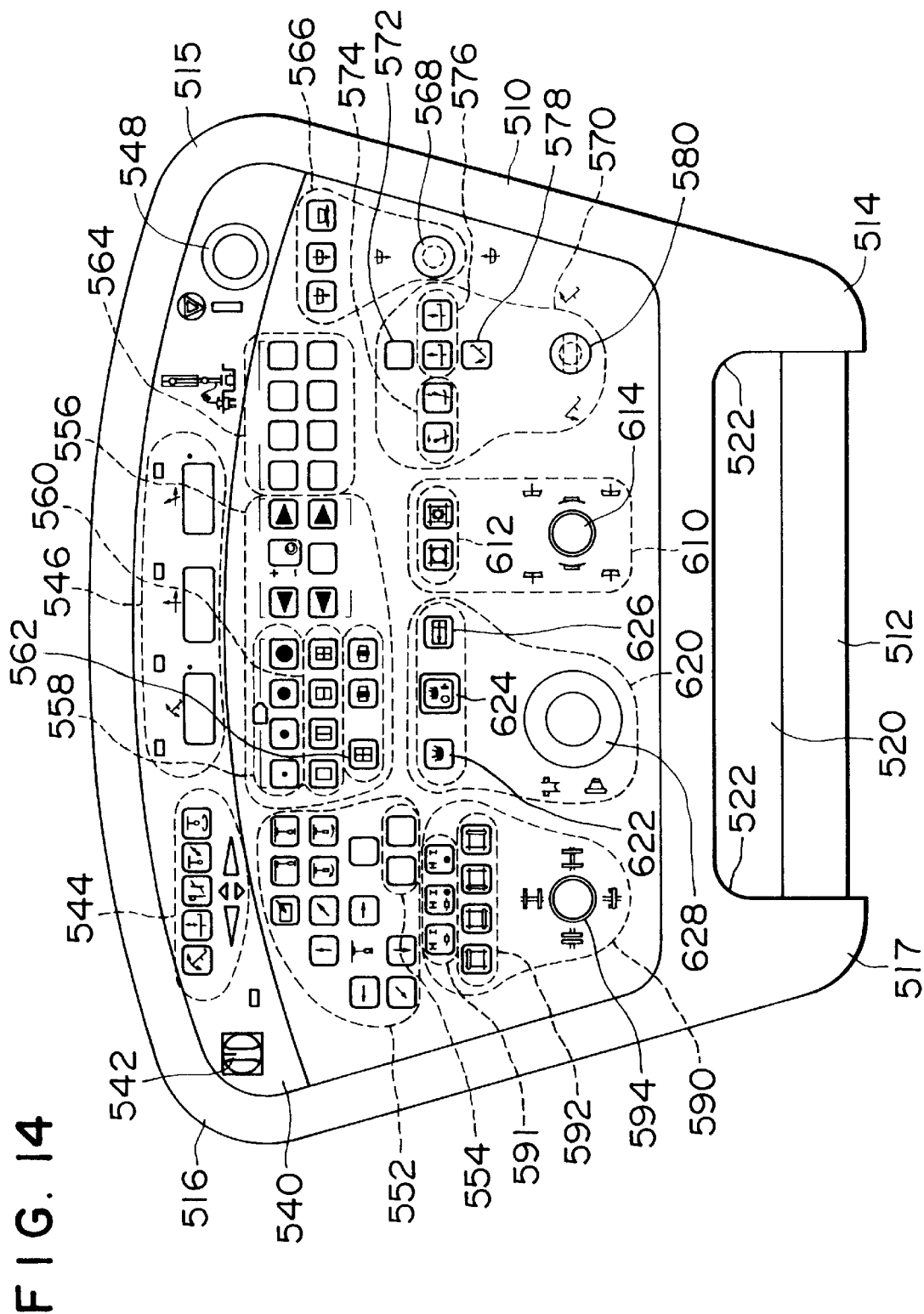
FIG. 14 is a front view showing the structure of a proximal operator console.

In FIG. 14, there is shown a photographing state display section 546 for displaying a photographing condition or state, said display section being disposed at the central portion of the rear portion 540 of the casing. Next to the display section, there is an interlock release display section 544 for showing an interlock release state. The display section is disposed to the outside, that is, the rear to make indications easily seen without being interrupted. There is a general locking switch 542 at the left end on the console. The switch 542 prevents an erroneous operation from occurring even if a switch or joy stick on the console is erroneously touched or struck by an object. Therefore, the switch has an advantage of enhancing the concentration of a doctor and nurses on medical treatment. An emergency switch 548 is provided at the right end on the console to be colored red. Upon pressing the switch, every operations stop. The switch 548 is located at the rear of the right end and easily recognized to be effective in accurate and quick operations.

A switch group 552 has a function for controlling the position of the X-ray irradiation section to enable setting a movement of the section along an X-direction rail or Y-direction rail, controlling an arm, and setting a height of the section. Switches 554 are used to set a height of the X-ray irradiation section at two preset levels of height. Either preset level of height of the X-ray irradiation section is selected by one of the switches 554, making it possible to automatically perform positioning of the section and perform a rapid and accurate operation of the section. A switch group 556 has a function for setting a X-ray photographing condition, and a switch group 558 makes it possible to selectively determine a size of the photographing section such as 16" or 12". A switch group 560 comprises selection switches for determining an arrangement of photographed images such as four images in one film or two images in one film. One of the monitor displays follows the above condition and the other of them displays enlargement. A switch group 562 is used to reverse an arrangement of a screen or top and bottom of the screen and enables operating displaying of a X-ray image and a photographed screen follows the operation. A switch group 564 has a function for controlling and setting automatic photographing. A switch group 590 has a function for controlling a diaphragming operation, a switch group 591 has a function for controlling translation of masks in the X and the Y directions, and a switch group 592 has a function for moving the respective mask independently, and a moving distance and a direction are controlled by a joy stick 594.

A switch group 610 has a function for determining a X-ray irradiation range referred to as filter and a switch group 612 determines whether to widen or narrow the irradiation range. The filter is provided in the X-ray irradiation section and performed by, for example, four diaphragm plates. Each of these diaphragm plates can be positioned by a joy stick 614. A switch group 570 has a function for controlling a relationship between the X-ray irradiation section and the bed, a switch group 576 has a function for controlling the vertical movement of the table 12, a switch group 574 has a function for keeping tilting of the table 12 as it is and changing only X-ray irradiation angles, and a switch 572 has a function for standing the table upright so that a person to be inspected is permitted to get on/off the table. A switch 578 has a function for lowering the head side portion of the table. Rotation, that is, tilting of the table can optionally be controlled by a joy stick. The table is tilted by operating both of the switch 578 and the joy stick 580 in order to prevent an erroneous operation, so that an erroneous operation due to collision of an object with the bed can be prevented to improve safety. A switch group 566 has a function for operating a compression pipe and a joy stick 568 has a function for optionally operating a compression cylinder. A switch group 620 has a function for taking X-ray photographing and a switch 622 has a function for attenuating a X-ray dose in confirming an image before photographing. Switches 624 and 626 have functions for adjusting a photographing timing and stopping X-ray irradiation after the lapse of a predetermined time. A joy stick 628 has a function for controlling a position of the light receiving section and comprises photographing instruction switches. Since the joy stick 628 also has the photographing instruction switches, photographing can be effected at the optimum timing which results in enhancement of accuracy and speed-up.

With the above arrangement, the joy stick is arranged this side and the operating switches are arranged next to the joy stick, so that final positioning and fine adjustment which are most frequently performed and most strain an operator's nerves are made easy due to the joy stick positioning this side. While the switch group 556 for initial setting is arranged on the back side, it is less frequently used and is operated at the start of inspection, which rarely strains an operator's nerves, and so the whole of the proximal operator console is made compact and ease in use.

Figure 17:
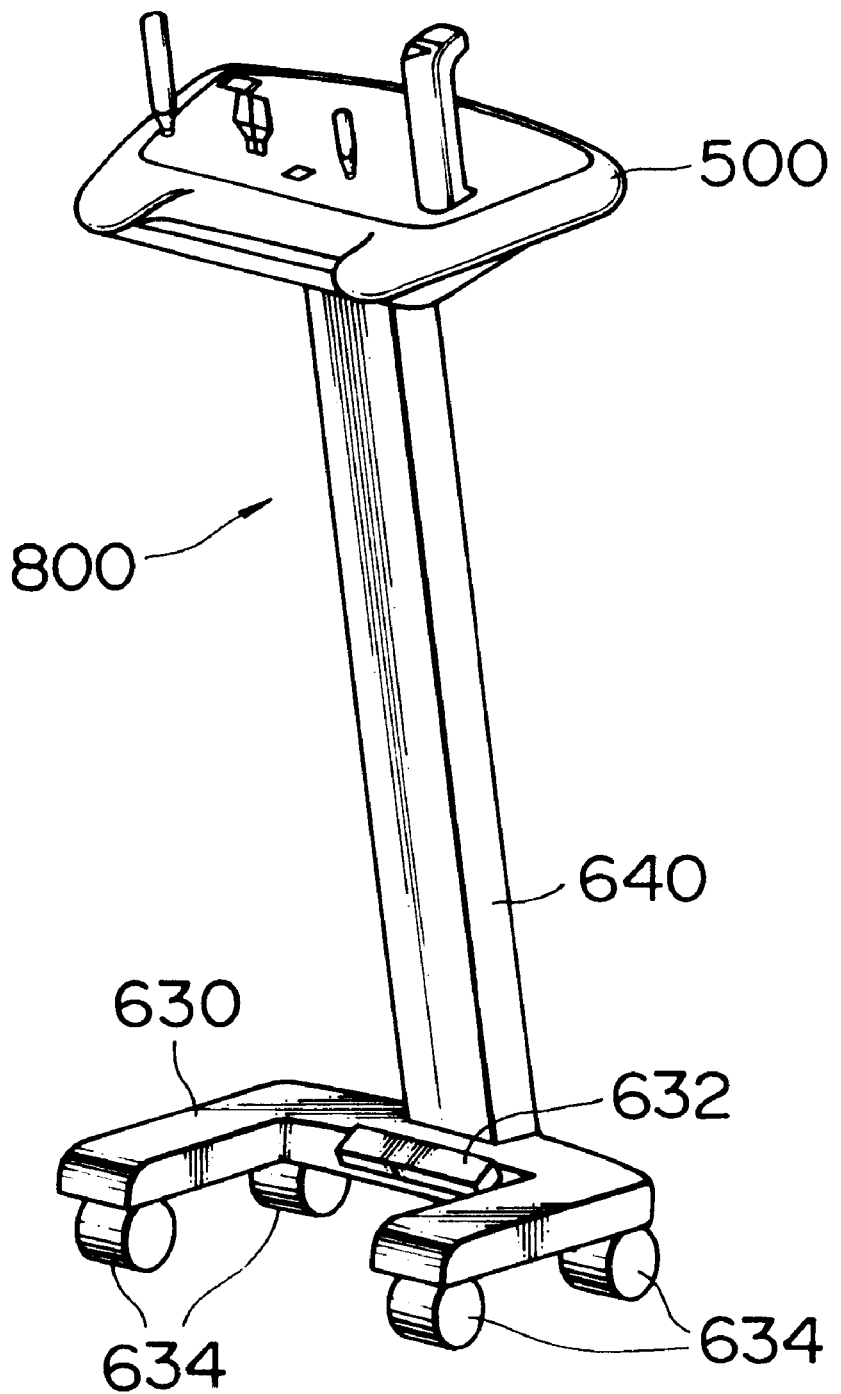
FIG. 17 is a front view showing a floor-type console having another structure of a proximal operator console.

FIG. 17 shows a floor-type proximal operator console 800 according to another embodiment. A strut 640 is mounted to a base 630 provided with four wheels 634 and the proximal operator console 500 is secured to the strut 640. Each of the four wheels 634 is mounted to be rotatable up to 360° as shown by the arrow. Moreover, the base 630 is provided with a foot switch 632 which has a function for irradiating slight X-rays in order to determine a photographing position. The top surface of the proximal operator console 500 has a height of 800 to 1,000 mm from the floor 2, which is suitable for a doctor or a technician to stand and operate the console.

An operation apparatus provided with the floor-type proximal operator console 800 has a similar advantage to that of the proximal operator console 500, which is an arm type and is stationary, and has the advantage described below. That is, the operation apparatus can be rapidly moved to a desired position by horizontally moving the floor-type console 800 which has a predetermined height.

Figure 18:
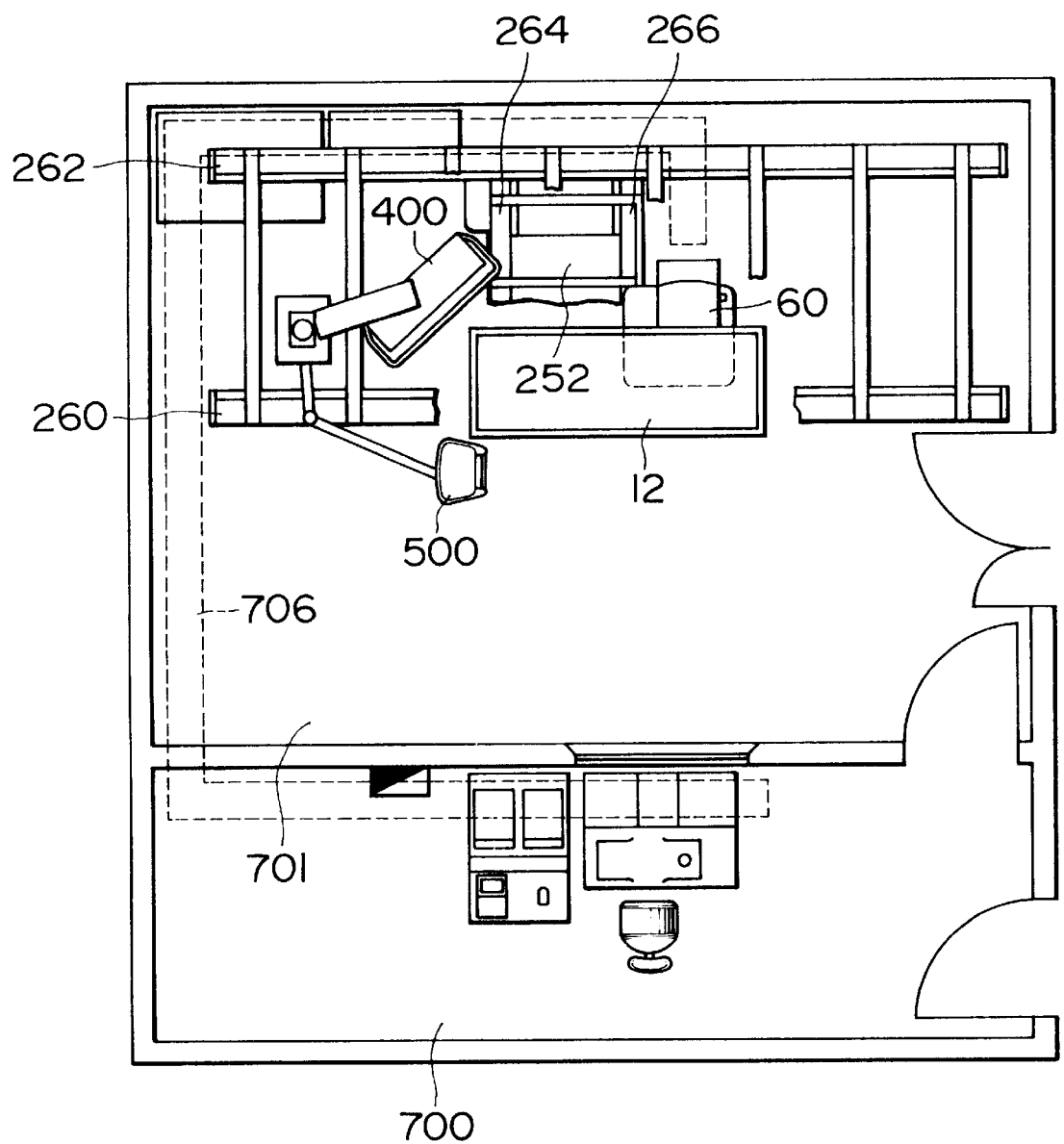
FIG. 18 a top view of a room showing the arrangement of a X-ray photographing apparatus of an embodiment of the present invention.

FIG. 18 is a top view as viewed from above the room, in which a photographing room 701 and a control room 700 are partitioned by a wall to permit operations to be performed on the other side of a window. A bed is placed in parallel with the wall and the X-direction rails 260 and 262 are secured to the ceiling in parallel with the X direction corresponding to a longitudinal direction of the bed. In this embodiment, the monitor 400 and the proximal operator console 500 are supported by the same X-direction rails 260 and 262. A dotted line 706 represents a signal line. The same X-direction rails 260 and 262 are used, so that the structure is simple and inexpensive as a whole. Moreover, a carriage 552 for the monitor 400 and the proximal operator console 500 is made safe since it is set to move in a range outside the moving range of the carriage 252 of the X-ray irradiation section. Moreover, an erroneous operation can be dealt with and safety is ensured since overrun detection switches are provided for preventing these moving ranges from being cleared.

Figure 19:
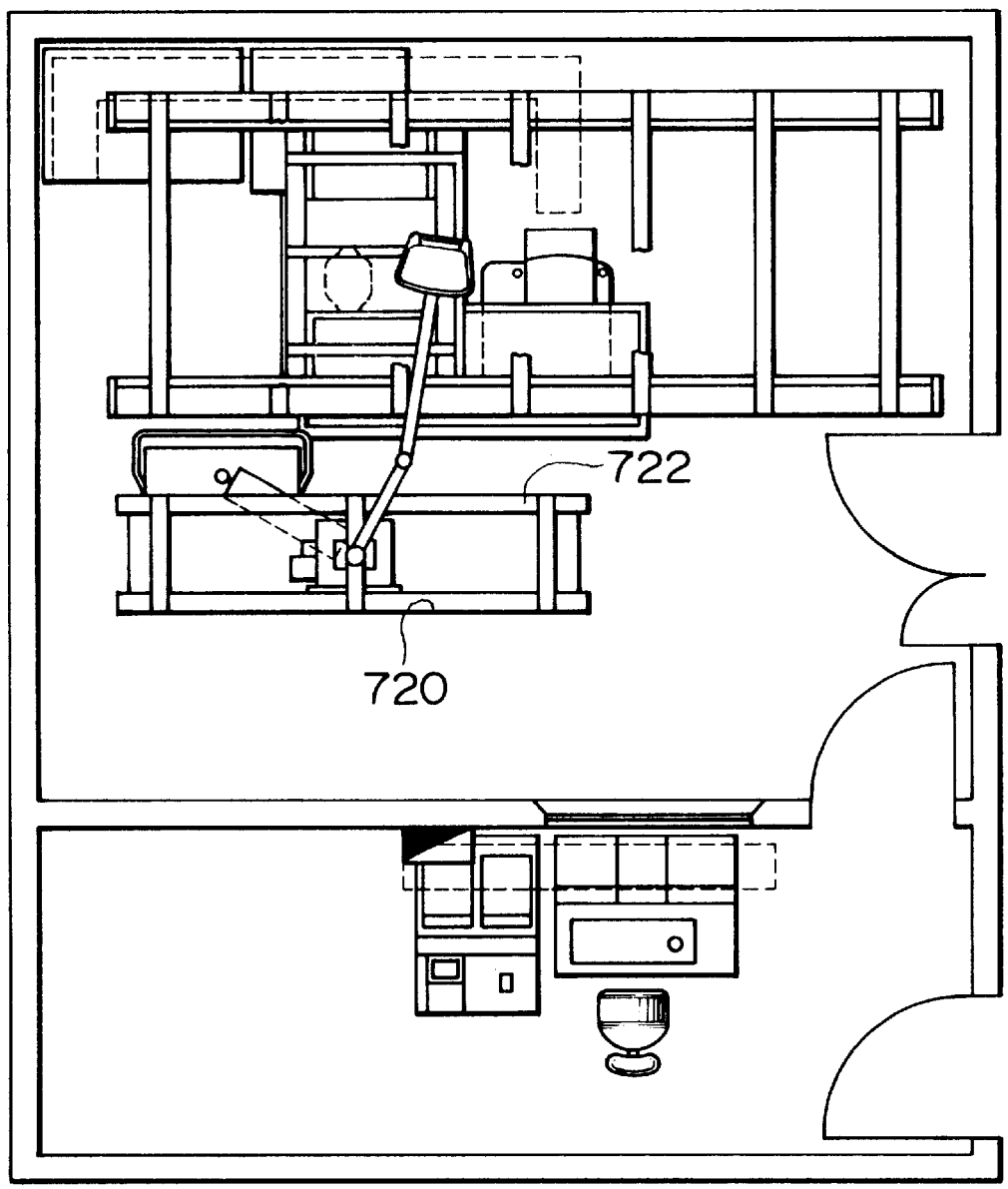
FIG. 19 is a top view of a room showing the arrangement of a X-ray photographing apparatus of another embodiment of the present invention.

FIG. 19 shows still another embodiment, in which the same symbol represents the same function, advantage, and object. In the embodiment, rails 720 and 722 for a monitor or a proximal operator console are provided in parallel with moving rails for a X-ray irradiation apparatus.

As described above, according to the present invention, a vertical support mechanism of the bed is arranged on one side of the bed and toward an end from a center in a longitudinal direction of a bed, for example, toward feet of a person to be inspected, so that the support mechanism will not interfere with a doctor who moves around a portion of the bed, where the upper half of the body of the person to be inspected is placed, and performs medical treatment, and a space for installation of other medical treatment equipments can be ensured.

What is claimed is:

1. An X-ray photographing apparatus comprising:
   a bed comprising a rectangular-shaped table for supporting a person to be inspected on a front surface thereof, a support mechanism supporting the table, and a base provided therein with a tilting mechanism for driving the support mechanism to tilt the table and arranged on one side of the table and offset a predetermined distance from a center of the bed in a longitudinal direction thereof toward the legs of the person to be inspected;
   an X-ray photographing device provided on a back surface of the table of the bed through a drive mechanism for moving the X-ray photographing device in longitudinal and lateral directions of the table;
   an X-ray source located above and separated from the bed;
   an X-ray source moving mechanism for moving the X-ray source in accordance with the tilting motion of the table and the movements of the X-ray photographing device so that the X-ray source and the X-ray photographing device face each other; and
   an operator console for controlling motions of the bed, the X-ray photographing device, the X-ray source moving mechanism and X-ray irradiation from the X-ray source toward the person to be inspected.

2. The X-ray photographing apparatus according to claim 1, wherein the base of the bed is provided with a drive mechanism for vertically moving the support mechanism.

3. The X-ray photographing apparatus according to claim 1, wherein the X-ray source moving mechanism comprises rail mechanisms provided on a ceiling in two directions, a carriage incorporated into one of the rail mechanisms, an extending and contracting mechanism extended downward from the carriage, and a rotating mechanism provided at a lower end of the extending and contracting mechanism for rotating the X-ray source.

4. The X-ray photographing apparatus according to claim 1, further comprising accessory mounting means including rail-shaped members mounted to recesses provided on longitudinal sides of the table.

5. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device supported from a ceiling, the X-ray irradiation device being located above the person to be inspected on the bed and spaced a distance from a top surface of the table, and an X-ray imaging device located below the table, said table support device being disposed outside a width of the table when the table is in a horizontal position and being settable to height which is smaller than a height of a top board of the bed.

6. The X-ray photographing apparatus according to claim 5, wherein the top surface of the table is settable to a height within a range of 600 to 1200 mm.

7. The X-ray photographing apparatus according to claim 5, wherein the top surface of the table is settable to have a height of 800 mm or less.

8. An X-ray photographing apparatus according to claim 5, further comprising a control panel provided in a operating room, said X-ray irradiation device, said bed and said X-ray imaging device being arranged in a photographing room, a window provided between said operating room and said photographing room, said bed being arranged so that an X-direction corresponding to the longitudinal direction of the bed is in parallel with said window, X-direction rails being arranged on the ceiling to be in parallel with said X-direction, Y-direction rails movable along said X-direction rails, and a support carriage movable along said X-direction rails, said X-ray irradiation section being mounted to said support carriage.

9. An X-ray photographing apparatus according to claim 5, further comprising X-direction rails mounted to the ceiling to be in parallel with an X-direction corresponding to the longitudinal direction of the bed, Y-direction rails movable along said X-direction rails, a support carriage movable along said X-direction rails, and guide rails mounted to said Y-direction rails, fitting portions provided on said support carriage to engage with said guide rails so that said fitting portions of said support carriage move along said Y-direction rails while engaging said guide rails, and said X-ray irradiation device being mounted to said support carriage.

10. The X-ray photographing apparatus according to claim 5, further comprising a rack provided on at least one of said Y-direction rails, a motor and a pinion rotated by the motor provided on said support carriage, and said rack and pinion engaging with each other.

11. The X-ray photographing apparatus according to claim 5, further comprising means for controlling movements of said X-ray imaging device, and means for controlling movements of said X-ray irradiation device, said X-ray imaging device and said X-ray irradiation device being movable together in a predetermined relation.

12. The X-ray photographing apparatus according to claim 5, further comprising means for effecting movement of at least one of the X-ray irradiation device and the X-ray imaging device in a predetermined manner.

13. The X-ray photographing apparatus according to claim 12, wherein the means for effecting movement includes rails provided on the ceiling, said X-ray irradiation device being movable along said rails.

14. The X-ray photographing apparatus according to claim 13, wherein the means for effecting movement further includes means for effecting movement of the X-ray imaging device so that the X-ray irradiation device and the X-ray imaging device are movable together in a predetermined relation.

15. An X-ray photographing apparatus comprising a table of a bed for mounting thereon a person to be inspected, a table support device having a function for tilting the table about an axis perpendicular to a longitudinal direction of the bed and vertically moving the table, an X-ray irradiation device located above the person to be inspected on the bed and spaced a distance from a top surface of the table, and an X-ray imaging device located below the table; and wherein said support device has a horizontal support for supporting the bed from the side of the bed and a vertical support mechanism for vertically moving said horizontal support and said vertical support mechanism is arranged on one side of the bed and is offset from a center of the bed in its longitudinal direction, further comprising a proximal operator console for operating at least one of said X-ray irradiation device, said table and said X-ray imaging device, and wherein a grip is provided at a front side of said proximal operator console.

16. An X-ray photographing apparatus comprising:
a bed comprising a rectangular-shaped table for supporting a person to be inspected on a front surface thereof, a support mechanism supporting the table, and a base provided therein with a tilting mechanism for driving the support mechanism to tilt the table and arranged on one side of the table and offset a predetermined distance from a center of the bed in a longitudinal direction thereof toward the legs of the person to be inspected;
an X-ray photographing device provided on a back surface of the table of the bed through a drive mechanism for moving the X-ray photographing device in longitudinal and lateral directions of the table;
an X-ray source located above the bed;
an X-ray source moving mechanism for moving the X-ray source in accordance with the tilting motion of the table and the movements of the X-ray photographing device so that the X-ray source and the X-ray photographing device face each other; and
an operator console for controlling motions of the bed, the X-ray photographing device, the X-ray source moving mechanism and X-ray irradiation from the X-ray source toward the person to be inspected.

17. The X-ray photographing apparatus according to claim 16, wherein an outer periphery of said casing is round and curved at portions thereof which extend from a front surface to a back surface.

18. The X-ray photographing apparatus according to claim 17, wherein a recess is formed on the back surface of the outer periphery of said casing.

19. The X-ray photographing apparatus according to claim 16, wherein a joy stick is provided at the front side of said operator console and operating switches are arranged on the back side of said operator console.

20. The X-ray photographing apparatus according to claim 16, wherein a display section is arranged on the back side of said operator console and a joy stick is arranged at the front side.

21. The X-ray photographing apparatus according to claim 16, wherein a display section is arranged on the back side of said operator console and an emergency stop switch is arranged at an end of the display section.

22. The X-ray photographing apparatus according to claim 16, wherein a display section is arranged on the back side of said operator console and a lock switch is arranged at an end of the display section.

23. The X-ray photographing apparatus according to claim 16, wherein the operator console comprises a casing which is narrow at a front side and wide on a back side thereof, a state display unit provided on the casing, an operating switch, and a joy stick for control.

24. An X-ray photographing apparatus comprising a table of a bed for mounting thereon a person to be inspected, a table support device having a function for tilting the table about an axis perpendicular to a longitudinal direction of the bed and vertically moving the table, an X-ray irradiation device located above the person to be inspected on the bed and spaced a distance from a top surface of the table, and an X-ray imaging device located below the table; and wherein said support device has a horizontal support for supporting the bed from the side of the bed and a vertical support mechanism for vertically moving said horizontal support and said vertical support mechanism is arranged on one side of the bed and is offset from a center of the bed in its longitudinal direction, further comprising a proximal operator console for operating at least one of said X-ray irradiation device, said table and said X-ray imaging device, and wherein said proximal operator console comprises a casing which is narrow at a front side and wide on a back side thereof, a state display unit provided on the casing, an operating switch, and a joy stick for control.

25. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device supported from a ceiling, the X-ray irradiation device being located above the person to be inspected on the bed and spaced a distance from a top surface of the table, an X-ray imaging device located below the table, said table support device being settable to height which is smaller than a height of a top board of the bed, and grip securing means provided on the sides of said table, wherein leg portions of grips extend along the side surfaces of the bed and are rotatably supported by said grip securing means.

26. An X-ray photographing apparatus according to claim 25, wherein at least portions of said grips toward an end of the bed where the head of the person to be inspected is positioned is tilted.

27. An X-ray photographing apparatus comprising a table of a bed for mounting thereon a person to be inspected, a table support device having a function for tilting the table about an axis perpendicular to a longitudinal direction of the bed and vertically moving the table, an X-ray irradiation device located above the person to be inspected on the bed and spaced a distance from a top surface of the table, and an X-ray imaging device located below the table, said table support device being offset toward a side where the legs of the person to be inspected are positioned, and an end of said table on a side where the head of the person to be inspected is positioned being cut at an underside thereof, and an end of said table on a side where the legs of the person to be inspected are positioned being substantially rectangular in shape.

28. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device located above the person to be inspected on the bed and spaced a distance from a top surface of the table, an X-ray imaging device located below the table, and an insertion port for insertion of X-ray photographing film being provided at an end of said table on a side where the head of the person to be inspected is positioned, the inserted X-ray photographing film being movable together with the X-ray imaging device in a longitudinal direction of the table.

29. A X-ray photographing apparatus comprising a X-ray irradiation section, a bed for mounting thereon a person to be inspected, a X-ray imaging device, X-direction rails provided on a ceiling to be in parallel with a X direction corresponding to a longitudinal direction of said bed, Y-direction rails movable along said X-direction rails, a support carriage movable along said Y-direction rails, said X-ray irradiation section being mounted to said support carriage, rails for a proximal operator console provided in parallel with said X-direction rails, a carriage for said proximal operator console arranged at said rails for said proximal operator-console, said proximal operator console being mounted to said carriage for said proximal operator-console.

30. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device located above the person to be inspected on the bed and spaced a distance from a top surface of the table, an X-ray imaging device located below the table, said table support device having a horizontal support for supporting the bed from the side of the bed and a vertical support mechanism for vertically moving said horizontal support, said vertical support mechanism being arranged on one side of the bed and is offset toward an end of the bed from a center of the bed in the longitudinal direction thereof, said table having a top board on the top surface thereof and rails provided on both side surfaces of said table for mounting thereto accessories, X-ray photographing film is inserted inside a space, said top board and said both side surfaces of said table delimiting a space from a side where the head of the person to be inspected is positioned where X-ray photographing film is inserted, the inserted X-ray photographing film being movable together with said X-ray imaging device in the longitudinal direction of said table.

31. An X-ray photographing apparatus comprising a table of a bed for mounting thereon a person to be inspected, a table support device having a function for tilting the table about an axis perpendicular to a longitudinal direction of the bed and vertically moving the table, an X-ray irradiation device located above the person to be inspected on the bed and spaced a distance from a top surface of the table, an X-ray imaging device located below the table, said table support device being offset toward a side where the legs of the person to be inspected are positioned in the longitudinal direction of the bed, said X-ray imaging device being movable in a longitudinal direction of the table, and an end of said table on a side where the head of the person to be inspected is positioned is cut at an underside thereof.

32. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device located above the person to be inspected on the bed and spaced a distance from a top surface of the table, an X-ray imaging device located below said table, said X-ray imaging device being movable in the longitudinal direction of said table, wherein when said X-ray imaging device is moved to a location on a side where the legs of the person to be inspected are positioned, from an end of the bed on a side where the head of the person to be inspected is positioned, an open space is defined at a location toward a side where the head of the person to be inspected is positioned, from said X-ray imaging device and below the bed.

33. The X-ray photographing apparatus according to claim 32, wherein said table support device is disposed at a location offset toward a side where the legs of the person to be inspected are positioned, from a center of the table in the longitudinal direction thereof, and an X-ray image receiving section of said X-ray imaging device is movable in a Y direction perpendicular to a X direction corresponding to the longitudinal direction of the bed.

34. The X-ray photographing apparatus according to claim 32, wherein a film changer is arranged in said open space.

35. An X-ray photographing apparatus comprising a table of a bed for mounting thereon a person to be inspected, a table support device having a function for tilting the table about an axis perpendicular to a longitudinal direction of the bed and for vertically moving the table, an X-ray irradiation device located above the person to be inspected on the bed and spaced a distance from a top surface of the table, an X-ray imaging device located below the table, a proximal operator console for operating at least one of said X-ray imaging device, said table and said X-ray imaging device, said proximal operator console being supported from a ceiling through an arm, said proximal operator console having narrow side at a front thereof and wide on a back side thereof.

36. An X-ray photographing apparatus comprising a table of a bed for mounting thereon a person to be inspected, a table support device having a function for tilting the table about an axis in a Y direction perpendicular to an X direction which corresponds to a longitudinal direction of the bed and vertically moving the table, an X-ray irradiation device located above the person to be inspected on the bed and spaced a distance from the top surface of the table, an X-ray imaging device located below the table, said table support device being settable to a height smaller than a height of the top surface of the table, said X-ray irradiation device having first guide portions respectively extending in the X direction and the Y direction of the bed so as to be movable in the X and the Y directions of said bed, said X-ray irradiation device and a driving motor for moving said X-ray irradiation device being suspended along said guide portions, and second guide portions extending in the X direction to move the X-ray image receiving section of said X-ray imaging device being respectively provided on the both sides of a lower portion of said table so as to move the X-ray image receiving section therealong in the x direction by said motor.

37. An X-ray photographing apparatus comprising an X-ray irradiation section, a bed for mounting thereon a person to be inspected, an X-ray imaging device, X-direction rails provided on a ceiling to be in parallel with an X direction corresponding to a longitudinal direction of said bed, Y-direction rails movable along said X-direction rails, a support carriage movable along said Y-direction rails, said X-ray irradiation section being mounted to said support carriage, and a proximal operator console, and a carriage for said proximal operator console being arranged in a position out of the moving range of said Y-direction rails along said X-direction rails, said proximal operator console being mounted on said carriage for said proximal operator console.

38. The X-ray photographing apparatus according to claim 37, wherein said Y rails have limit switches for detecting a range of a safety area, and said proximal operator console is mounted out of said safety area.

39. An X-ray photographing apparatus comprising a substantially rectangular-shaped bed having a table for mounting thereon a person to be inspected, a horizontal support offset from the center of the bed for supporting the bed perpendicularly to a longitudinal direction of the bed, a mechanism for maintaining said horizontal support at a specified level, a rotating angle support device provided on an underside of the bed for supporting the bed at a specified angle relative to the horizontal support, and an X-ray irradiation device and an X-ray imaging device provided with the bed therebetween, the X-ray irradiation device being supported from a ceiling, the level maintaining mechanism acting to change a level of the bed, and rotating angle support device acting to change an inclination of the bed, wherein the horizontal support, the level maintaining mechanism and the rotating angle support device are disposed outside a width of the table when the table is in a horizontal position and are settable to a height which is smaller than a height of a top board of the bed.

* * * * *